(12) United States Patent
Tong et al.

(10) Patent No.: US 12,337,360 B2
(45) Date of Patent: Jun. 24, 2025

(54) SYSTEMS AND METHODS FOR CLEANING SURFACES OF A WORKPIECE

(71) Applicant: GM GLOBAL TECHNOLOGY OPERATIONS LLC, Detroit, MI (US)

(72) Inventors: Stanley Tong, Ferndale, MI (US); Jeffrey B Harris, Detroit, MI (US); Brennon L White, Novi, MI (US); Adam John Campbell, Rochester, MI (US); Andrew Thomas Cunningham, Cambridge, MA (US); Ali Shabbir, Windson (CA)

(73) Assignee: GM GLOBAL TECHNOLOGY OPERATIONS LLC, Detroit, MI (US)

( * ) Notice: Subject to any disclaimer, the term of this patent is extended or adjusted under 35 U.S.C. 154(b) by 484 days.

(21) Appl. No.: 17/817,314

(22) Filed: Aug. 3, 2022

(65) Prior Publication Data

US 2024/0042496 A1   Feb. 8, 2024

(51) Int. Cl.
*B08B 5/04*     (2006.01)
*A61K 31/205*   (2006.01)
(Continued)

(52) U.S. Cl.
CPC .............. *B08B 5/04* (2013.01); *A61K 31/205* (2013.01); *A61K 31/519* (2013.01); *A61K 31/59* (2013.01);
(Continued)

(58) Field of Classification Search
CPC ........... B08B 5/04; B08B 5/02; B25J 11/0085
See application file for complete search history.

(56) References Cited

U.S. PATENT DOCUMENTS

2017/0239893 A1* 8/2017 Hoover ................. B29C 64/393
2019/0315065 A1* 10/2019 Hutchinson ............ B29C 64/35
(Continued)

FOREIGN PATENT DOCUMENTS

DE     102006049541 A1     8/2017
DE     102017206815 A1 *  10/2018
(Continued)

OTHER PUBLICATIONS

DE 102021213174 A1—English Machine Translation (Year: 2023).*
DE 102021213791 A1—English Machine Translation (Year: 2023).*

*Primary Examiner* — Marc Carlson
(74) *Attorney, Agent, or Firm* — Lorenz & Kopf LLP

(57) ABSTRACT

Systems and methods are provided for cleaning surfaces of a workpiece. The system includes a housing defining an enclosure, a holding structure within the enclosure that is configured to support a workpiece, a first powder removal device that is configured to propel a first media toward the holding structure such that the first media contacts the workpiece while the workpiece is supported by the holding structure, a first sensing device that is configured to detect surface characteristics of the workpiece while the workpiece is supported by the holding structure, and a controller configured to, by a processor: detect a powder material on a surface of the workpiece based on the surface characteristics, and selectively operate the first powder removal device to remove the powder material from the surface with the first media while the workpiece is supported by the holding structure.

20 Claims, 5 Drawing Sheets

(51) Int. Cl.
    *A61K 31/519*     (2006.01)
    *A61K 31/59*     (2006.01)
    *A61K 31/714*     (2006.01)
    *A61K 33/06*     (2006.01)
    *A61K 33/26*     (2006.01)
    *A61K 45/06*     (2006.01)
    *B25J 11/00*     (2006.01)

(52) U.S. Cl.
    CPC ............ *A61K 31/714* (2013.01); *A61K 33/06* (2013.01); *A61K 33/26* (2013.01); *A61K 45/06* (2013.01); *B25J 11/0085* (2013.01)

(56) References Cited

U.S. PATENT DOCUMENTS

| | | | |
|---|---|---|---|
| 2020/0122391 A1* | 4/2020 | Hertling | B29C 64/379 |
| 2023/0067017 A1* | 3/2023 | Salfity | B29C 64/35 |
| 2023/0321727 A1* | 10/2023 | Vogtmeier | B22F 3/16 |
| | | | 75/228 |

FOREIGN PATENT DOCUMENTS

| | | | | |
|---|---|---|---|---|
| DE | 102021213174 A1 * | 5/2023 | ............. | B08B 5/02 |
| DE | 102021213791 A1 * | 6/2023 | ............. | B29C 64/35 |
| WO | 2019152064 A1 | 8/2019 | | |
| WO | 2021173135 A1 | 9/2021 | | |
| WO | 2022048957 A1 | 3/2022 | | |

* cited by examiner

SYSTEMS AND METHODS FOR CLEANING SURFACES OF A WORKPIECE

INTRODUCTION

The technical field generally relates to workpiece surface cleaning systems, and more particularly relates to systems and methods for removing a powder build material from a workpiece produced by an additive manufacturing process.

Additive manufacturing is a group of processes characterized by manufacturing three-dimensional components by building up substantially two-dimensional layers (or slices) on a layer-by-layer basis. Each layer is generally very thin (for example between about 20 to about 100 microns) and many layers are formed in a sequence with the two-dimensional shape varying on each layer to provide the desired final three-dimensional profile. In contrast to traditional "subtractive" manufacturing processes where material is removed to form a desired component profile, additive manufacturing processes progressively add material to form a net shape or near net shape final component.

In an additive-manufacturing process, a model, such as a design model, of the component may be defined in any suitable manner. For example, the model may be designed with computer-aided design (CAD) software. The model may include three-dimensional (3D) numeric coordinates of the entire configuration of the component including both external and internal surfaces. The model may include several successive two-dimensional (2D) cross-sectional slices that together form the 3D component.

Powder bed fusion (PBF) is a subset of additive manufacturing whereby a heat source (e.g., laser, thermal print head) is used to consolidate material in powder form to form three-dimensional (3D) objects. The heat source is applied to particles contained within a powder bed, which gradually indexes down as each layer is completed and new powder is spread over the build area. Advantages of PBF include cost-effective customization, reduced assembly, and an ability to produce complex geometries without support structures. However, a potential drawback of PBF relates to removal of the component from the powder bed after production of the component. Often, unfused powder remains on surfaces of the component and may be trapped in fine channels and recesses. Such residual powder must be removed prior to further processing and/or use of the component.

Accordingly, it is desirable to provide systems and/or methods capable of removing residue, unfused powder from surfaces of components formed by certain additive manufacturing techniques, such as PBF. Furthermore, other desirable features and characteristics of the present invention will become apparent from the subsequent detailed description and the appended claims, taken in conjunction with the accompanying drawings and the foregoing technical field and background.

SUMMARY

A system is provided for cleaning a surface of a workpiece. In one embodiment, the system includes a housing defining an enclosure, a holding structure within the enclosure, the holding structure configured to support a workpiece, a first powder removal device within the enclosure, the first powder removal device configured to propel a first media toward the holding structure such that the first media contacts the workpiece while the workpiece is supported by the holding structure, a first sensing device within the enclosure, the first sensing device configured to detect surface characteristics of the workpiece while the workpiece is supported by the holding structure, and a controller configured to, by a processor: detect a powder material on a surface of the workpiece based on the surface characteristics, and selectively operate the first powder removal device to remove the powder material from the surface with the first media while the workpiece is supported by the holding structure.

In an embodiment, the controller of the system is configured to, by the processor, selectively move the first powder removal device relative to the workpiece as supported by the holding structure.

In an embodiment, the holding structure of the system includes a basket configured to releasable retain the workpiece therein, and the controller is configured to move the first powder removal device around the basket, wherein the basket includes a plurality of openings configured to allow passage therethrough of the first media.

In an embodiment, the holding structure of the system includes a first robotic arm configured to support and move the workpiece, the frame includes a second robotic arm configured to support and move the first powder removal device, and the controller is configured to, by the processor: selectively operate the first robotic arm to move the workpiece relative to the first powder removal device and/or the first sensing device, and selectively operate the second robotic arm to move the first powder removal device relative to the workpiece.

In an embodiment, the controller of the system is configured to, by the processor, selectively move the first sensing device relative to the workpiece as supported by the holding structure.

In an embodiment, the system includes additional powder removal devices within the enclosure, each of the additional powder removal devices are configured to propel a corresponding one of additional media toward the holding structure such that the corresponding one of the additional media contacts the workpiece while the workpiece is supported on the holding structure, wherein the controller is configured to, by the processor, selectively operate the additional powder removal devices independently to remove the powder material from the surface with the additional media while the workpiece is supported by the holding structure, wherein each of the first media and the additional media are different.

In an embodiment, the system includes additional sensing devices within the enclosure, each of the additional sensing devices are configured to detect one or more additional surface characteristics of the workpiece while the workpiece is supported on the holding structure, wherein the controller is configured to, by the processor, detect the powder material on the surface of the workpiece based on the additional surface characteristics, wherein each of the first sensing device and the additional sensing devices comprise different sensing technology.

In an embodiment, the system includes a suction device configured to generate a suction force sufficient to extract the powder material and the first media through an outlet of the enclosure. In an embodiment, the system includes a separation device configured to receive the powder material and the first media from the outlet of the enclosure and automatically separate the powder material and the first media.

In an embodiment, the workpiece is produced by a powder-based additive manufacturing process.

A method is provided for cleaning a surface of a workpiece. In one embodiment, the method includes supporting the workpiece with a holding structure within an enclosure of a housing, sensing surface characteristics of the workpiece with a first sensing device within the enclosure while the workpiece is supported by the holding structure, detecting, by a processor, a powder material on a surface of the workpiece based on the surface characteristics, and selectively operating, by the processor, a first powder removal device within the enclosure to propel a first media toward the holding structure such that the first media contacts the workpiece while the workpiece is supported by the holding structure and thereby remove the powder material from the surface.

In an embodiment, the method includes selectively controlling, by the processor, a frame within the enclosure supporting the first powder removal device to move the first powder removal device relative to the workpiece as supported by the holding structure.

In an embodiment, supporting the workpiece with the holding structure includes retaining the workpiece in a basket of the holding structure, the method including selectively controlling, by the processor, the frame to move the first powder removal device around the basket while operating the first powder removal device to propel the first media through a plurality of openings of the basket to contact the workpiece.

In an embodiment, the method includes supporting the workpiece with a first robotic arm of the holding structure, supporting the first powder removal device with a second robotic arm, selectively operating, by the processor, the first robotic arm to move the workpiece relative to the first powder removal device and/or the first sensing device, and selectively operating, by the processor, the second robotic arm to move the first powder removal device relative to the workpiece.

In an embodiment, the method includes selectively controlling, by the processor, a frame within the enclosure supporting the first sensing device supported thereby to move the frame relative to the workpiece as supported by the holding structure.

In an embodiment, the method includes selectively operating, by the processor, additional powder removal devices within the enclosure to propel additional media toward the holding structure such that the additional media contacts the workpiece while the workpiece is supported by the holding structure and thereby remove the powder material from the surface, wherein each of the first media and the additional media are different.

In an embodiment, the method includes sensing additional surface characteristics of the workpiece with additional sensing devices within the enclosure while the workpiece is supported by the holding structure, and detecting, by the processor, the powder material on the surface of the workpiece based on the additional surface characteristics, wherein each of the first sensing device and the additional sensing devices comprise different sensing technology.

In an embodiment, the method includes generating a suction force sufficient to extract the powder material removed from the workpiece and the first media subsequent to the first media contacting the workpiece through an outlet of the enclosure with a suction device. In an embodiment, the method includes receiving the powder material and the first media from the outlet of the enclosure with a separation device, and automatically separating the powder material and the first media with the separation device.

In an embodiment, the method includes producing the workpiece by a powder-based additive manufacturing process.

BRIEF DESCRIPTION OF THE DRAWINGS

The exemplary embodiments will hereinafter be described in conjunction with the following drawing figures, wherein like numerals denote like elements, and wherein.

DETAILED DESCRIPTION

Figure 1:
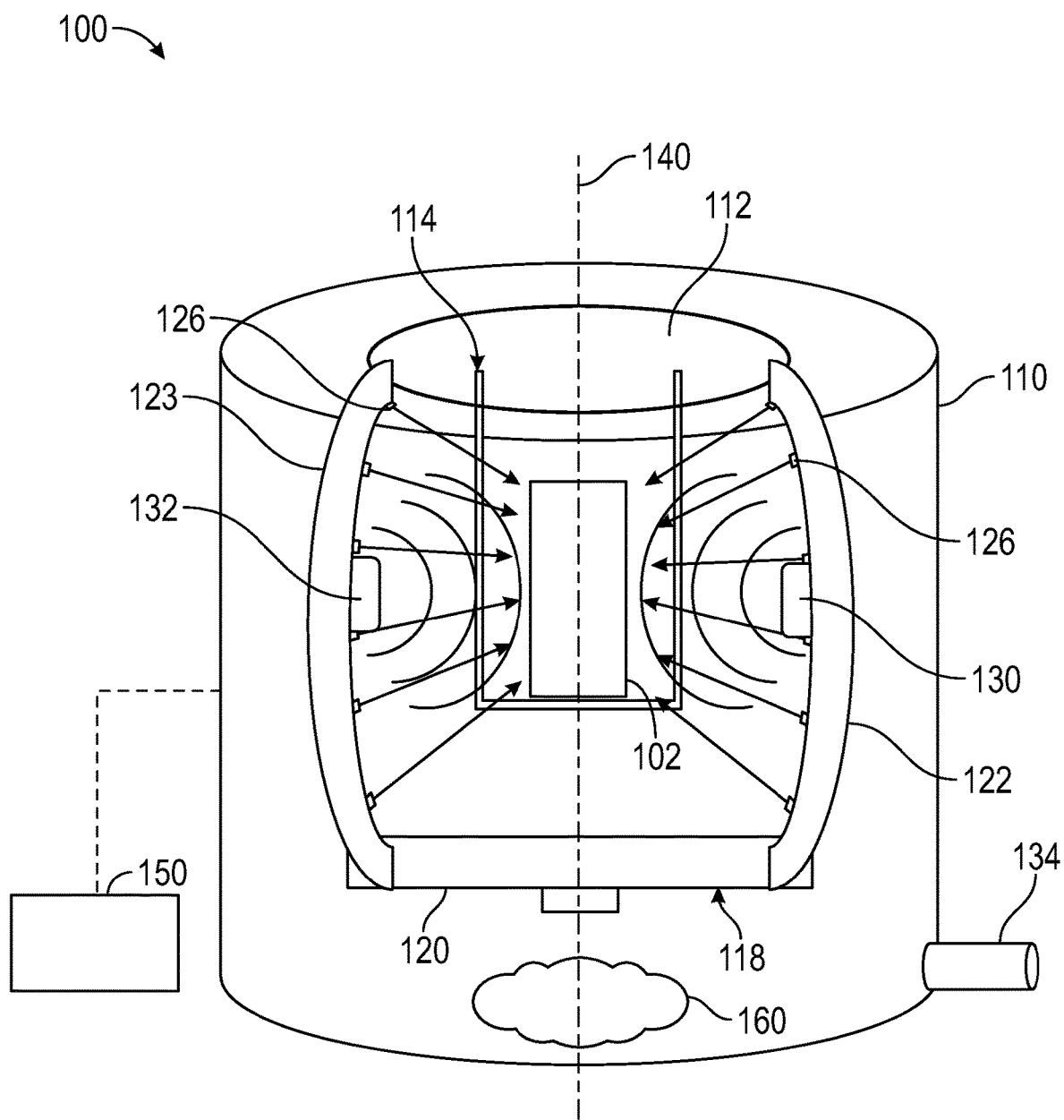
FIG. 1 is simplified cross-sectional view of a first depowdering system in accordance with an embodiment.

The following detailed description is merely exemplary in nature and is not intended to limit the application and uses. Furthermore, there is no intention to be bound by any expressed or implied theory presented in the preceding technical field, background, brief summary or the following detailed description. As used herein, the term module refers to any hardware, software, firmware, electronic control component, processing logic, and/or processor device, individually or in any combination, including without limitation: application specific integrated circuit (ASIC), an electronic circuit, a processor (shared, dedicated, or group) and memory that executes one or more software or firmware programs, a combinational logic circuit, and/or other suitable components that provide the described functionality.

Embodiments of the present disclosure may be described herein in terms of functional and/or logical block components and various processing steps. It should be appreciated that such block components may be realized by any number of hardware, software, and/or firmware components configured to perform the specified functions. For example, an embodiment of the present disclosure may employ various integrated circuit components, e.g., memory elements, digital signal processing elements, logic elements, look-up tables, or the like, which may carry out a variety of functions under the control of one or more microprocessors or other control devices. In addition, those skilled in the art will appreciate that embodiments of the present disclosure may be practiced in conjunction with any number of systems, and that the systems described herein is merely exemplary embodiments of the present disclosure.

For the sake of brevity, conventional techniques related to signal processing, data transmission, signaling, control, and other functional aspects of the systems (and the individual operating components of the systems) may not be described in detail herein. Furthermore, the connecting lines shown in the various figures contained herein are intended to represent example functional relationships and/or physical couplings between the various elements. It should be noted that many alternative or additional functional relationships or physical connections may be present in an embodiment of the present disclosure.

Various systems and methods are provided herein for automatically cleaning surfaces of a workpiece by contact between the surfaces and one or more cleaning media. In some embodiments, the workpiece is a component produced by a powder-based additive manufacturing process, such as but not limited to a powder bed fusion (PBF) process wherein the component is formed from and within a bed of build material in powder form. In such embodiments, the systems and methods are configured to remove the residue, unfused build material (hereinafter the "powder material") from the surfaces of the component. Although certain embodiments discussed herein are in relation to removing the powder material from components formed by additive manufacturing processes, the systems and methods are not limited to such applications, and may be used for cleaning surfaces of workpieces produced by other means, such as certain subtractive manufacturing processes, for example, by removing various debris, material waste (e.g., shavings), manufacturing chemicals, and other materials present on the surfaces of the workpieces.

Referring initially to FIG. 1, a first depowdering system 100 is presented in accordance with a nonlimiting embodiment. The first depowdering system 100 includes a housing 110 that defines an enclosure, a holding structure 114, a frame 118, a first powder removal device 122, a second powder removal device 123, a first sensing device 130, and a second sensing device 132 within the enclosure, and a controller 150.

The housing 110 includes walls having interior surfaces that, in combination, define the enclosure. In FIG. 1, the walls of the housing 110 define a cylinder-shaped enclosure; however, the housing 110 is not limited to any particular configuration, and other shapes are envisioned for the enclosure. In some embodiments, the housing 110 includes an access panel 112 configured to open to allow access into the enclosure through an opening thereof, for example, for insertion of a workpiece 102 into the enclosure, and configured to close and seal the opening thereof to impede access to the enclosure, for example, subsequent to insertion of the workpiece 102. Although the access panel 112 is represented as having a circular shape and being located in an upper wall of the housing 110 in FIG. 1, the access panel 112 is not limited to any particular configuration or location.

The holding structure 114 is configured to support the workpiece 102 within the enclosure. In some embodiments, the holding structure 114 is configured to support the workpiece 102 in an elevated position within the enclosure. In various embodiments, the holding structure 114 includes a basket having a primary opening configured to allow the workpiece 102 to be received within the basket, and a plurality of holes in walls of the basket configured to provide passage of cleaning media therethrough. In FIG. 1, the holding structure 114 is represented as having a cylindrical shape; however, the holding structure 114 is not limited to any particular configuration.

The frame 118 includes a base 120 with the first powder removal device 122 and the second powder removal device 123 extending from the base 120 on opposite sides of the holding structure 114. The base 120 is configured to rotate about an axis of rotation 140 thereof such that the first powder removal device 122 and the second powder removal device 123 move about the workpiece 102 while supported in the holding structure 114. With this arrangement, each of the first powder removal device 122 and the second powder removal device 123 are provided with line-of-sight to various surfaces of the workpiece 102 as the base 120 of the frame 118 rotates. Although the first depowdering system 100 is presented as including two powder removal devices, the first depowdering system 100 may include fewer or more powder removal devices.

The first powder removal device 122 and the second powder removal device 123 are configured to propel a first media and a second media, respectively, toward the holding structure 114 such that the first media and/or the second media contacts the workpiece 102 while the workpiece 102 is supported by the holding structure 114, for example retained within the basket of the holding structure 114. Upon contact with the workpiece 102, the first media and the second media are configured to remove the powder material thereon, for example, due to impact forces, abrasion, or other various means. In embodiments that include additional powder removal devices (i.e., more than two), each of the powder removal devices may optionally be configured to propel a different media.

In FIG. 1, the first powder removal device 122 and the second powder removal device 123 each include a plurality of nozzles 126 secured thereto. The first media and the second media may be provided to the respective nozzles 126 such that the first media and the second media are sprayed toward the workpiece 102 while supported by the holding structure 114. In some embodiments, the first media and the second media are provided to the respective nozzles 126 via passages internal to the first powder removal device 122 and the second powder removal device 123, respectively, or via tubing secured to the first powder removal device 122 and the second powder removal device 123, respectively. The nozzles 126 or the first powder removal device 122 and the second powder removal device 123 may be arranged such that the first media and the second media are directed toward the workpiece 102 at various angles. For example, FIG. 1 represents the first powder removal device 122 and the second powder removal device 123 as having a concave profile relative to the holding structure 114. As such, the nozzles 126 thereof are oriented such that the first media and the second media are propelled therefrom at angles dependent on the location of the individual nozzles 126 along the first powder removal device 122 and the second powder removal device 123. The directions of the propelled media are represented in FIG. 1 by arrows. In other embodiments, the nozzles 126 may be movable along the first powder removal device 122 and the second powder removal device 123. Although FIG. 1 represents each of the first powder removal device 122 and the second powder removal device 123 as including six nozzles 126, the first depowdering system 100 may include more or fewer nozzles 126, apertures, or other components suitable for propelling the one or more cleaning media.

Various cleaning media may be used by the first powder removal device 122 and the second powder removal device 123. The cleaning media may include one or more gases, liquids, solids, or combinations thereof. The cleaning media may have various compositions, mixtures, material properties, and physical properties. Nonlimiting examples of cleaning media include inert liquids (e.g., water), inert gases (e.g., carbon dioxide), and mixtures thereof.

The first sensing device 130 and the second sensing device 132 are configured to sense, detect, and/or monitor surface characteristics of the workpiece 102 while the workpiece 102 is supported by the holding structure 114. The first sensing device 130 and the second sensing device 132 may utilize various sensing technologies to detect the surface characteristics. Surface characteristics may include certain physical and material properties such as, but are not limited to, surface color, reflectance, hardness, composition, texture, and geometric dimensions. Exemplary sensing technologies that may be used to sense one or more of the surface characteristics include light scanning, surface reflectivity, IR spectrography, and ultrasound technologies. In one example, the first sensing device 130 or the second sensing device 132 may detect a color of the surface of the workpiece 102 and such color may be compared to a baseline color to determine if the powder material remains on the surface. In another example, the first sensing device 130 or the second sensing device 132 may use ultrasonic sensors to detect a density of the surface of the workpiece 102 and such density may be comparted to a baseline density to determine if the powder material remains on the surface. In yet another example, the first sensing device 130 or the second sensing device 132 may use a visual camera to capture images and/or video of the surface of the workpiece 102 and such images or video may be comparted to baseline images or video to determine if the powder material remains on the surface. In some embodiments, manual feedback may be used to determine if the powder material remains on the surface. Although the first depowdering system 100 is presented as including two sensing devices, the first depowdering system 100 may include fewer or more sensing devices. In embodiments that include additional sensing devices (i.e., more than two), each of the sensing devices may optionally be configured to utilize different sensing technologies.

In FIG. 1, the first sensing device 130 and the second sensing device 132 are secured to the first powder removal device 122 and the second powder removal device 123, respectively. However, it should be understood that the first sensing device 130 and the second sensing device 132 may be located elsewhere within the enclosure, such as coupled to other portions of the frame 118. In addition, the first depowdering system 100 may include fewer or more sensing devices within the disclosure each utilizing the same or different sensing technologies.

The controller 150 is functionally coupled to the various components of the first depowdering system 100 and configured to selectively operate, by one or more processors, the various components, including one or more of the frame 118, the first powder removal device 122, the second powder removal device 123, the first sensing device 130, and the second sensing device 132. In some embodiments, the controller 150 is configured to, by the processor, selectively operate the first sensing device 130 and/or the second sensing device 132 to sense the surface characteristics, receive the surface characteristics, detect the powder material on the surface of the workpiece 102 based on the surface characteristics, and selectively operate the first powder removal device 122 and/or the second powder removal device 123 to remove the powder material from the surface with the first media and/or the second media, respectively, while the workpiece 102 is supported by the holding structure 114. In some embodiments, the controller 150 is configured to, by the processor, selectively operate the frame 118 within the enclosure to move the first powder removal device 122 and/or the second powder removal device 123 supported thereby relative to the holding structure 114.

The controller 150 includes at least one processor, a communication bus, and a computer readable storage device or media. The processor can be any custom made or commercially available processor, a central processing unit (CPU), a graphics processing unit (GPU), an auxiliary processor among several processors associated with the controller 150, a semiconductor-based microprocessor (in the form of a microchip or chip set), a macroprocessor, any combination thereof, or generally any device for executing instructions. The computer readable storage device or media may include volatile and nonvolatile storage in read-only memory (ROM), random-access memory (RAM), and keep-alive memory (KAM), for example. KAM is a persistent or non-volatile memory that may be used to store various operating variables while the processor is powered down. The computer-readable storage device or media may be implemented using any of a number of known memory devices such as PROMs (programmable read-only memory), EPROMs (electrically PROM), EEPROMs (electrically erasable PROM), flash memory, or any other electric, magnetic, optical, or combination memory devices capable of storing data, some of which represent executable instructions, used by the controller 150 in controlling the system first depowdering system 100. The bus serves to transmit programs, data, status and other information or signals between the various components of the first depowdering system 100. The bus can be any suitable physical or logical means of connecting computer systems and components. This includes, but is not limited to, direct hard-wired connections, fiber optics, infrared, and wireless bus technologies.

The instructions may include one or more separate programs, each of which comprises an ordered listing of executable instructions for implementing logical functions. The instructions, when executed by the processor, receive and process signals from the sensing devices, perform logic, calculations, methods and/or algorithms for automatically removing the powder material from surfaces of the workpiece 102 based on the logic, calculations, methods, and/or algorithms. Although only one controller 150 is shown in FIG. 1, embodiments of the first depowdering system 100 can include any number of controllers that communicate over any suitable communication medium or a combination of communication mediums and that cooperate to process the sensor signals, perform logic, calculations, methods, and/or algorithms.

In various embodiments, one or more instructions of the controller 150 are embodied in the first depowdering system 100 and, when executed by the processor, receive data from the first sensing device 130 and the second sensing device 132 and process the data in order to remove the powder material and/or debris from the surfaces of the workpiece 102.

As can be appreciated, that the controller 150 may otherwise differ from the embodiment depicted in FIG. 1. For example, the controller 150 may be coupled to or may otherwise utilize one or more remote computer systems and/or other control systems, for example as part of one or more of the above-identified devices and systems. It will be appreciated that while this exemplary embodiment is described in the context of a fully functioning computer system, those skilled in the art will recognize that the mechanisms of the present disclosure are capable of being distributed as a program product with one or more types of non-transitory computer-readable signal bearing media used to store the program and the instructions thereof and carry out the distribution thereof, such as a non-transitory computer readable medium bearing the program and containing computer instructions stored therein for causing a computer processor to perform and execute the program. Such a program product may take a variety of forms, and the present disclosure applies equally regardless of the particular type of computer-readable signal bearing media used to carry out the distribution. Examples of signal bearing media include recordable media such as floppy disks, hard drives, memory cards and optical disks, and transmission media such as digital and analog communication links. It will be appreciated that cloud-based storage and/or other techniques may also be utilized in certain embodiments. It will similarly be appreciated that the computer system of the controller 150 may also otherwise differ from the embodiment depicted in FIG. 1, for example in that the computer system of the controller 150 may be coupled to or may otherwise utilize one or more remote computer systems and/or other control systems.

Figure 2:
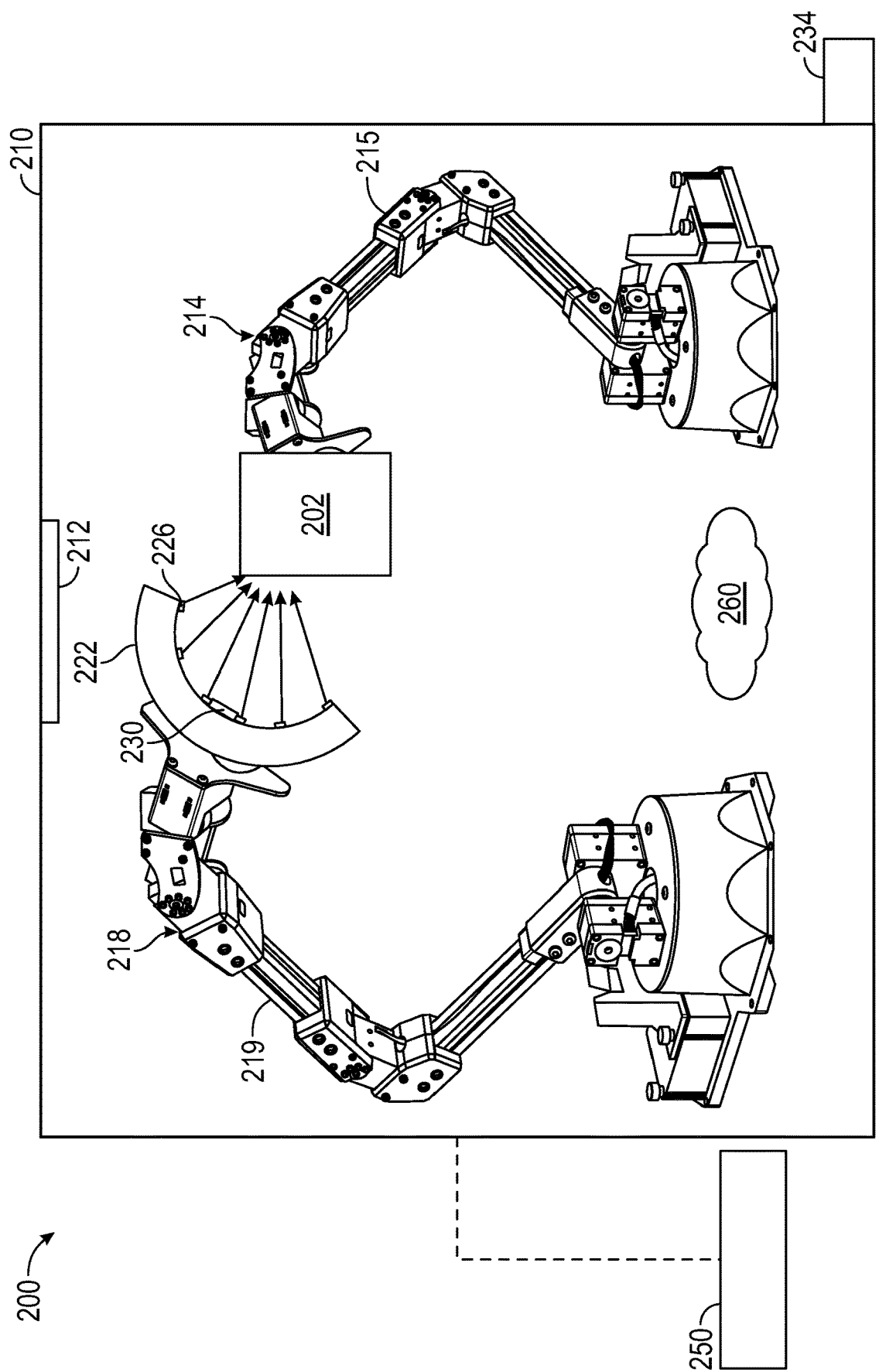
FIG. 2 is a simplified cross-sectional view of a second depowdering system in accordance with an embodiment.

FIG. 2 represents a second depowdering system 200 in accordance with another embodiment. In view of similarities between the first and second embodiments, the following discussion of FIG. 2 will focus primarily on aspects of the second embodiment that differ from the first embodiment in some notable or significant manner. Other aspects of the second embodiment not discussed in any detail can be, in terms of structure, function, materials, etc., essentially as was described for the first embodiment. For convenience, consistent reference numbers are used to identify the same or functionally related elements, but with a numerical prefix (e.g., 2) added to distinguish the second embodiment from the first embodiment of FIG. 1.

As with the first embodiment of FIG. 1, the second depowdering system 200 includes a housing 210 having interior surfaces that, in combination, define an enclosure. In the second embodiment, a holding structure 214 within the housing 210 includes a first robotic arm 215 and the frame 218 includes at least a second robotic arm 219 that are both located within the enclosure. As used herein, the term robotic arm refers to and/or includes a programmable or controllable mechanical arm that includes two or more links coupled by a joint configured for rotational motion or translational (linear) displacement) that in combination define a kinematic chain. The first robotic arm 215 and the second robotic arm 219 each include an end effector having one or more tools for direct or indirect interaction with the workpiece 202. Although the holding structure 214 and the frame 218 of the second depowdering system 200 each include a single robotic arm, either of the holding structure 214 and the frame 218 may include one or more additional robotic arms.

The first robotic arm 215 is configured to releasably support and selectively move the workpiece 202. The first robotic arm 215 may include various tools or mounting systems suitable for supporting the workpiece 202. In various embodiments, the first robotic arm 215 includes a gripper, that is, an impactive jaw, claw, or other structure configured to physically grasp the workpiece 202 by direct contact.

The second robotic arm 219 is configured to support and selectively move a first powder removal device 222 and a first sensing device 230. As previously mentioned, the frame 218 may include any number of robotic arms, such as a third robotic arm configured to support and selectively move a second powder removal device and a second sensing device. In other embodiments, the first sensing device 230 and the second sensing device are supported by additional robotic arms and/or fixed structures independent from the first robotic arm 215 and any other robotic arms that include powder removal devices.

The first robotic arm 215 and the second robotic arm 219 may have various configurations and capabilities and therefore are not limited to any particular structure. For example, the first robotic arm 215 and the second robotic arm 219 may have 3-axes of articulation or more (i.e., degrees of freedom), such as 4-axes, 5-axes, 6-axes, or 7-axes. In an embodiment, the first robotic arm 215 and the second robotic arm 219 are each 6-axis robotic arms configured for independent movement in x, y, and z planes, as well as roll, pitch, and yaw movements.

In various embodiments, movement and operation of the first robotic arm 215 and the second robotic arm 219 are controlled by a controller 250 to perform a cleaning process. In various embodiments, the controller 250 is configured to, by a processor: selectively operate the first robotic arm 215 to move the workpiece 202 relative to the first powder removal device 222 and/or the first sensing device 230, and selectively operate the second robotic arm 219 to move the first powder removal device 222 and/or the first sensing device 230 relative to the workpiece 202. Control of the first robotic arm 215 and the second robotic arm 219 may be based on a spatial coordinate system, such as a Cartesian coordinate system and, if relevant, Cartesian transformations (e.g., joint angles of the end effectors) which may be preprogrammed and/or determined by the controller 250. The movement of the first robotic arm 215 and the second robotic arm 219 may be achieved, for example, via control signals from the controller 250 that control various components of the first robotic arm 215 and the second robotic arm 219, such as actuators (e.g., servo motors) configured to move the joints thereof. Additional details of the construction, operation, and function of first robotic arm 215 and the second robotic arm 219 are well known in the art and therefore will not be described in further detail herein.

Other components of the second depowdering system 200 of FIG. 2, such as the first powder removal device 222, the first sensing device 230, and the controller 250 may be configured and operated in substantially similar manners as described above in relation to the first embodiment of FIG. 1.

The second embodiment of FIG. 2 may provide for more precise powder removal relative to the first embodiment of FIG. 1. For example, movement of the first robotic arm 215 and the second robotic arm 219 relative to one another may allow for direct line-of-sight between one or more nozzles 226 of the first powder removal device 222 and surfaces of the workpiece 202 that require powder removal.

Figure 3:
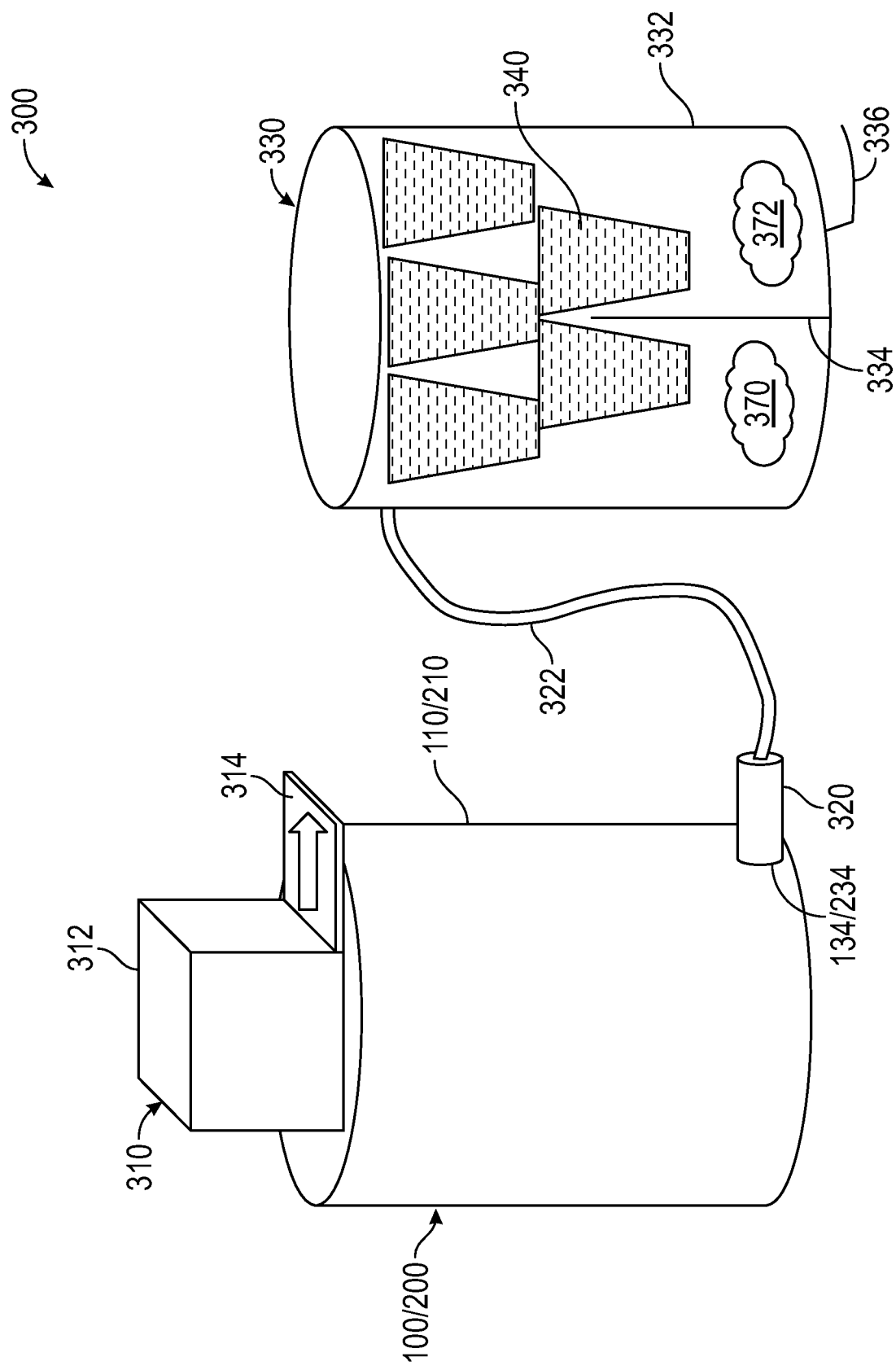
FIG. 3 is a simplified cross-sectional view of a workpiece cleaning system that includes a depowdering system, such as those presented in FIGS. 1 and 2, in accordance with an embodiment.

Referring now to FIG. 3 and with continued reference to FIGS. 1-2, certain aspects of an exemplary cleaning system 300 are provided that incorporate a depowdering system, such as the first depowdering system 100 or the second depowdering system 200. In various embodiments, the cleaning system 300 includes a cooling unit 310, a suction device 320, and a separation unit 330.

The cooling unit 310 includes a housing 312 having walls that in combination define an enclosed cavity therebetween. After producing the workpiece 102/202, the workpiece 102/202 may be inserted into the cavity of the housing 312. The cooling unit 310 is configured to reduce a temperature of the workpiece 102/202, actively or passively, prior to insertion into the housing 110/210 through the access panel 112/212. The cooling unit 310 may include a release panel 314 that is operable to open and close a passage between the cooling unit 310 and the access panel 112/212 of the depowdering system 100/200.

The suction device 320 is coupled with the outlet 134/234 of the depowdering system 100/200 and is configured to generate a suction force sufficient to extract a mixture 160/260 comprising the powder material, the first media, and/or the second media through the outlet 134/234 of the enclosure. In various embodiments, the suction device 320 generates sufficient suction force at the outlet 134/234 to produce a low-pressure environment within the enclosure of the depowdering system 100/200, that is, an environment having a pressure less than an ambient environment outside of the housing 110/210 (e.g., less than about 1 atm or 101.325 kPa). The suction device 320 may include, but is not limited to, an air amplifier, a vacuum pump, or another device capable of generating a suction force.

During the depowdering process, the first media and/or the second media may be sprayed to remove the powder material and/or debris on the surface of the workpiece 102/202. Subsequently, the sprayed first media and/or second media, as well as the removed powder material and/or debris may fall from the workpiece 102/202, through the basket of the holding structure 114 (if present), and toward a base of the housing 110/210. As previously noted, air flow and/or a low-pressure environment may be generated within the enclosure to direct the falling substances toward one or more outlets of the housing 110/210 to remove the substances continuously or periodically from the enclosure.

In various embodiments, the removed mixture 160/260 of the substances may be transported to the separation unit 330, for example, via a conduit 322. The separation unit 330 is configured to receive the mixture 160/260 from the outlet 134/234 of the enclosure and automatically separate the substances of the mixture 160/260 into separate compartments, containers, vessels, or the like. For example, the mixture 160/260 may be processed to separate the powder material, the first media, the second media, the debris, etc. As a nonlimiting example, FIG. 3 represents the mixture 160/260 as separated into the first media (identified at 370) and the powder material (identified at 372). In various embodiments, the separation unit 330 is configured to separate the powder material into reusable powder material and non-reusable powder material. Once separated, the various substances may be reused, recycled, or disposed of as desired. The separation unit 330 includes a housing 332 having walls that in combination device an enclosure therebetween and, for example, separation walls 334 within the enclosure. The separation unit 330 may include various structures within the enclosure that are configured for separation of the substances of the mixture 160/260, such as but not limited to a filtration system 340, a cyclone system, a centrifuge system, etc.

Figure 4:
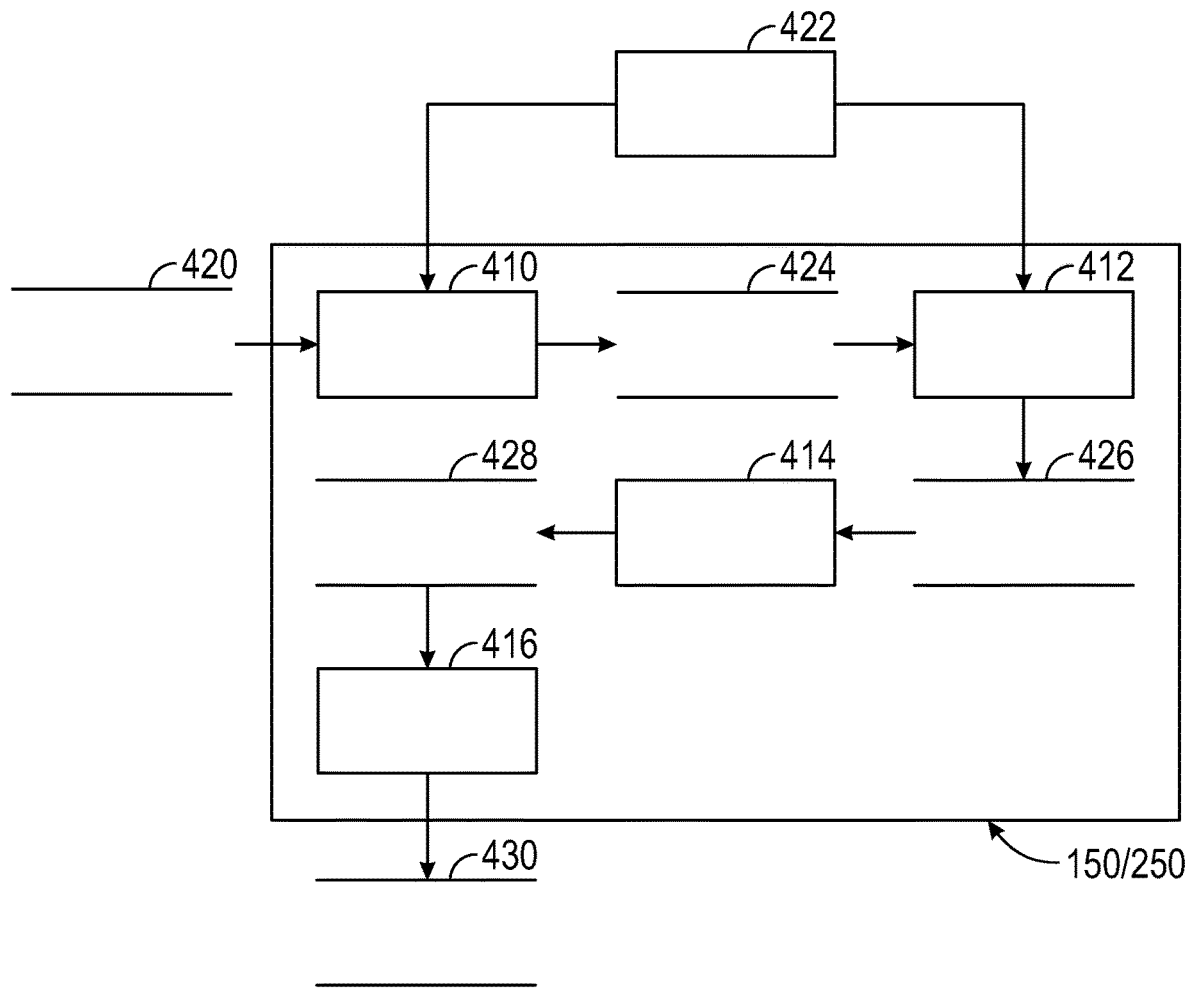
FIG. 4 is a dataflow diagram illustrating elements of the depowdering systems of FIGS. 1 and 2, in accordance with various embodiments.

With reference to FIG. 4 and with continued reference to FIGS. 1-3, a dataflow diagram illustrates elements of the first and second depowdering systems 100/200 of FIGS. 1-3 in accordance with various embodiments. As can be appreciated, various embodiments of the depowdering systems 100/200 according to the present disclosure may include any number of modules embedded within the controller 150/250 which may be combined and/or further partitioned to similarly implement systems and methods described herein. Furthermore, inputs to the depowdering systems 100/200 may be received from other control modules (not shown) and/or determined/modeled by other sub-modules (not shown) within the controller 150/250. Furthermore, the inputs might also be subjected to preprocessing, such as sub-sampling, noise-reduction, normalization, feature-extraction, missing data reduction, and the like. In various embodiments, the depowdering systems 100/200 includes an identification module 410, an analysis module 412, a cleaning module 414, and a control module 416.

In various embodiments, the identification module 410 receives as input workpiece data 420 and/or sensor data 422. In various embodiments, the workpiece data 420 includes various information relating to the workpiece 102/202, such as predetermined dimensions, materials, and the like. In some embodiments, the workpiece data 420 includes schematics of the workpiece 102/202 provided in, for example, computer-aided design (CAD) format used for production of the workpiece 102/202. In various embodiments, the sensor data 422 includes various information generated by one or more of the sensing devices 130,132/230 and includes information relating to the sensed surface characteristics of the workpiece 102/202.

The identification module 410 analyzes the workpiece data 420 and/or the sensor data 422 to identify the workpiece 102/202. In various embodiments, the workpiece data 420 may directly provide an identity of the workpiece 102/202. In various embodiments, the identification module 410 compares the surface characteristics to baseline information relating to various workpieces contained in the workpiece data 420 such as shape, dimensions, etc. to determine a closest match between the baseline information and the surface characteristics.

In various embodiments, the analysis module 412 receives as input identification data 424 and/or the sensor data 422. The identification data 424 includes various information generated by the identification module 410 such as the baseline information.

The analysis module 412 analyses the sensor data 422 to determine whether the powder material and/or debris is present on surfaces of the workpiece 102/202. In various embodiments, the analysis module 412 detects the powder material by comparing the sensor data 422 to the baseline information of the identification data 424. For example, the sensor data 422 may include measured dimensions of the surface of the workpiece 102/202 and the analysis module 412 may compare the measured dimensions to baseline dimensions of the baseline information. As another example, the sensor data 422 may include sensed colors of the surface of the workpiece 102/202 and the analysis module 412 may compare the sensed colors to baseline colors of the baseline information. As yet another example, the sensor data 422 may include sensed compositions of the surface of the workpiece 102/202 and the analysis module 412 may compare the sensed compositions to baseline compositions of the baseline information. As a more specific example, the baseline information may indicate that a recess on a surface of the workpiece 102/202 should be 2 mm deep and the surface characteristics may indicate that the recess is only 1.5 mm deep. In this example, the analysis module 412 may determine that the recess contains 0.5 mm of the powder material therein.

In various embodiments, the cleaning module 414 receives as input surface data 426 that includes various information generated by the analysis module 412. In various embodiments, the surface data 426 includes information relating to surfaces of the workpiece 102/202 that have the powder material thereon. In some embodiments, the surface data 426 includes information relating to a difference in the surface characteristics relative to the baseline information. In some embodiments, the surface data 426 includes coordinates corresponding to locations of the powder material on the surfaces of the workpiece 102/202. In some embodiments, the surface data 426 may include thicknesses of the powder material on the surfaces of the workpiece 102/202.

The cleaning module 414 analyzes the surface data 426 and determines a cleaning process for the workpiece 102/202. In various embodiments, the cleaning process may be one of a plurality of preprogrammed cleaning processes, for example, specific to the workpiece 102/202, specific to the workpiece geometry, or specific to a geometry of a surface of the workpiece 102/202. In various embodiments, the cleaning process may be generated by the cleaning module 414 based on the surface data 426 and include, for example, specific surfaces of the workpiece 102/202 to be cleaned and/or cleaning details associated with the specific surfaces such as a cleaning media to be used, a pressure of the cleaning media to be used, a spray direction of the cleaning media to be used (e.g., which nozzles 126/226 to use), a duration of the cleaning media spraying, etc.

In various embodiments, the control module 416 receives as input cleaning data 428 that includes various information relating to the cleaning process as determined by the cleaning module 414. In various embodiments, the cleaning data 428 may include steps and operating parameters of the components of the depowdering system 100/200 for implementing the cleaning process.

The control module 416 analyzes the cleaning data 428 and generates control data 430 configured to control operation of the various components of the depowdering system 100/200 to execute the cleaning process. In some embodiment, the control data 430 includes information relating to desired movement of the holding structure 114/214 (if applicable), desired movement of the frame 118/218, desired application of the cleaning media via the powder removal devices 122/123/222, and/or desired sensing of the surfaces of the workpiece 102/202 via the sensing devices 130/132/230.

Figure 5:
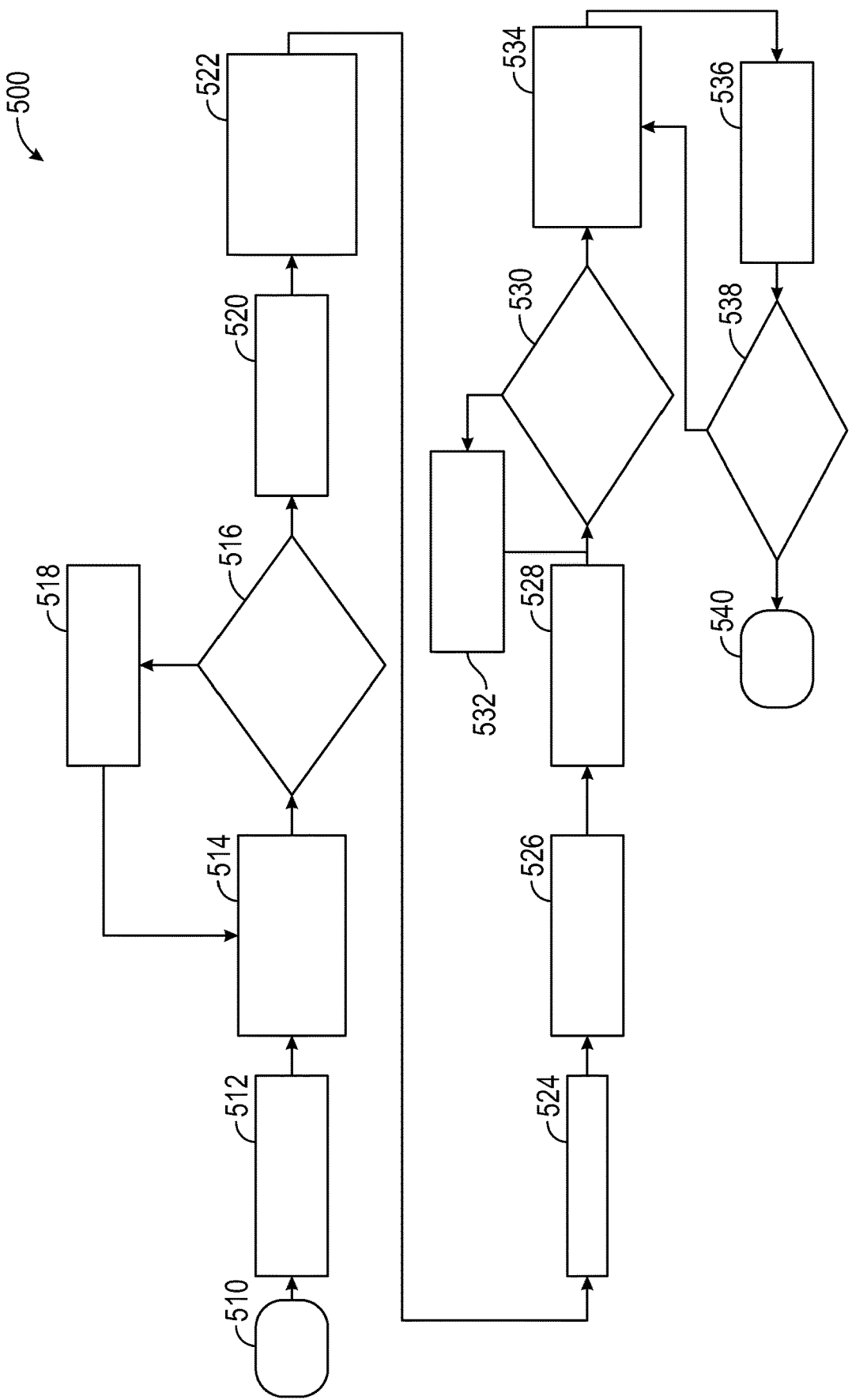
FIG. 5 is a flowchart of a process for cleaning a workpiece as performed by the first depowdering system of FIG. 1 or the second depowdering system of FIG. 2, in accordance with exemplary embodiments.

With reference now to FIG. 5 and with continued reference to FIGS. 1-4, a flowchart provides a method 500 for removing trace and/or residual powder material from a workpiece 102/202 as performed by the depowdering system 100/200, in accordance with exemplary embodiments. As can be appreciated in light of the disclosure, the order of operation within the method 500 is not limited to the sequential execution as illustrated in FIG. 5 but may be performed in one or more varying orders as applicable and in accordance with the present disclosure.

In one example, the method 500 may begin at 510. The method 500 may include a design stage in which the workpiece 102/202 is created, for example, in a computer-aided design (CAD) format. The workpiece 102/202 is analyzed at 514 to determine whether the workpiece 102/202 as designed is identifiable and depowderable. The workpiece 102/202 may be identifiable, for example, due to a structure (e.g., geometry, color, etc.) that is sufficiently different from other workpieces to be identified using the sensing devices 130/132/230, or by identification markings provided thereon such as a barcode, numerical code, product name, logo, etc. that may be correlated to a database of various identification markings. The workpiece 102/202 may be depowderable if the structure allows for sufficient removal of the powder material by the depowdering system 100/200. Workpieces determined to not be depowderable may have structures that are not capable of being inserted into the enclosure, being supported by the holding structure 114/214, or having all surfaces thereof accessible and cleanable by the powder removal devices 122/123/222 (e.g., inaccessible cavities, deep channels, etc.).

If the workpiece 102/202 is determined at 518 to not be identifiable and/or depowderable, the workpiece 102/202 may be redesigned or modified at step 518 and the redesigned workpiece 102/202 may be analyzed again at 514. Once the workpiece 102/202 has been determined to be identifiable and depowderable at 518, the workpiece 102/202 may be produced by an additive manufacturing process at 520.

Once the workpiece 102/202 has been produced, the method 500 may include a pre-cleaning stage in which the workpiece 102/202 undergoes an initial cleaning process. The initial cleaning process may be generic to all workpieces or may be specific to the workpiece 102/202 but not necessarily specific to any particular amount of the powder material on any surface of the workpiece 102/202. At 522, the workpiece 102/202 may be located within the system 100/200, for example, by inserting the workpiece 102/202 through the access panel 112/212 and supporting the workpiece 102/202 with the holding structure 114/214 within the enclosure. Alternatively, the initial cleaning process may be performed on the workpiece 102/202 with another depowdering system configured to remove at least some of the powder material and/or debris from surfaces of the workpiece 102/202.

The initial cleaning process is performed on the workpiece 102/202, either individually or simultaneously with other workpieces, at 524. In various embodiments, the initial cleaning process may be configured to clean surfaces of the workpiece 102/202 in a manner that promotes subsequent identification of the workpiece 102/202. For example, the initial cleaning may include removing some or substantially all the powder material from a surface of the workpiece 102/202 that includes an identification marking. At 526, the workpiece 102/202 may be oriented in a position suitable for subsequent identification, if necessary.

The method 500 continues to a preparation stage wherein the workpiece 102/202 is identified at 528. Once the identity of the workpiece 102/202 is determined, the orientation of the workpiece 102/202 may be analyzed at 530. If the workpiece 102/202 requires reorientation for subsequent cleaning, the workpiece 102/202 may be repositioned at 532.

Once a determination has been made that the workpiece 102/202 is ready for cleaning, the method 500 continues to a cleaning stage. At 534, a cleaning schedule may be determined and/or generated for the workpiece 102/202. The cleaning schedule may include cleaning instructions generic to the workpiece 102/202 or may include cleaning instructions that are specific to individual surfaces of the workpiece 102/202. The cleaning process (identified in FIG. 5 as the workpiece specific cleaning) is performed on the workpiece 102/202 in accordance with the cleaning schedule at 536. In various embodiments, the cleaning process may include selectively operating one or more of the powder removal devices 122/123/222 within the enclosure to propel the cleaning media toward the holding structure 114/214 such that the cleaning media contacts the workpiece 102/202 while the workpiece 102/202 is supported by the holding structure 114/214 and thereby remove the powder material from the surface. In various embodiments, the cleaning process may include selectively controlling the frame 118/218 within the enclosure supporting the powder removal device 122/123/222 to move the powder removal device 122/123/222 relative to the holding structure 114/214. In various embodiments, the cleaning process may include selectively controlling the frame 118/218 within the enclosure supporting one or more of the sensing devices 130/132/230 to move the sensing device(s) 130/132/230 relative to the holding structure 114/214. In various embodiments, the cleaning process may include selectively controlling the holding structure 114/214, if applicable, within the enclosure supporting the workpiece 102/202 to move the workpiece 102/202 relative to the powder removal device(s) 122/123/222 and/or the sensing device(s) 130/132/230.

In various embodiments, the method 500 may include generating a suction force sufficient to extract the mixture 160/260 comprising the powder material removed from the workpiece 102/202 and/or the cleaning media through the outlet 134/234 of the enclosure with the suction device 320. In various embodiments, the method 500 may include receiving the mixture 160/260 from the outlet 134/234 of the enclosure with the separation unit 330, and automatically separating the powder material and/or the cleaning media of the mixture 160/260 with the separation unit 330.

Once the cleaning process is complete, the workpiece 102/202 is analyzed at 538 to determine whether the surfaces of the workpiece 102/202 are clean, that is, substantially free of the powder material and/or debris, or if the workpiece 102/202 requires additional cleaning. For example, analysis of the workpiece 102/202 may include sensing the surface characteristics of the workpiece 102/202 with the sensing device 130/132/230 within the enclosure while the workpiece 102/202 is supported by the holding structure 114/214. The powder material may be detected on the surface of the workpiece 102/202 based on the surface characteristics.

If the powder material is detected on the surfaces of the workpiece 102/202 at 538, an additional cleaning schedule may be determined and/or generated at 534 and the workpiece 102/202 may be cleaned in accordance with the additional cleaning schedule. This process may be repeated as desired until the workpiece 102/202 is clean. In various embodiments, the detection of the powder material on surfaces of the workpiece 102/202 may be compared to a threshold to determine if additional cleaning is desired. Once a determination has been made that the workpiece 102/202 is sufficiently clean, the workpiece 102/202 may be removed from the depowdering system 100/200 and the method may end at 540.

While at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability, or configuration of the disclosure in any way. Rather, the foregoing detailed description will provide those skilled in the art with a convenient road map for implementing the exemplary embodiment or exemplary embodiments. It should be understood that various changes can be made in the function and arrangement of elements without departing from the scope of the disclosure as set forth in the appended claims and the legal equivalents thereof.

What is claimed is:

1. A system, comprising:
   a housing defining an enclosure;
   a holding structure within the enclosure, the holding structure configured to support a workpiece;
   a first powder removal device within the enclosure, the first powder removal device configured to propel a first media toward the holding structure such that the first media contacts the workpiece while the workpiece is supported by the holding structure;
   a first sensing device within the enclosure, the first sensing device configured to detect surface characteristics of the workpiece while the workpiece is supported by the holding structure;
   a controller configured to, by a processor:
     detect a powder material on a surface of the workpiece based on the surface characteristics; and
     selectively operate the first powder removal device to remove the powder material from the surface with the first media while the workpiece is supported by the holding structure;
   a suction device configured to generate a suction force sufficient to extract the powder material and the first media through an outlet of the enclosure; and
   a separation device configured to receive the powder material and the first media from the outlet of the enclosure and to automatically separate the powder material and the first media, wherein the powder material is further separated into a reusable powder material and a non-reusable powder material.

2. The system of claim 1, wherein the controller is configured to, by the processor, selectively move the first powder removal device relative to the workpiece as supported by the holding structure.

3. The system of claim 2, wherein the holding structure includes a basket configured to retain the workpiece therein, and the controller is configured to move the first powder removal device around the basket, wherein the basket includes a plurality of openings configured to allow passage therethrough of the first media.

4. The system of claim 2, wherein the holding structure includes a first robotic arm configured to support and move the workpiece, a second robotic arm configured to support and move the first powder removal device, and the controller is configured to, by the processor:
   selectively operate the first robotic arm to move the workpiece relative to the first powder removal device and/or the first sensing device; and
   selectively operate the second robotic arm to move the first powder removal device relative to the workpiece.

5. The system of claim 1, wherein the controller is configured to, by the processor, selectively move the first sensing device relative to the workpiece as supported by the holding structure.

6. The system of claim 1, further comprising additional powder removal devices within the enclosure, each of the additional powder removal devices are configured to propel a corresponding one of additional media toward the holding structure such that the corresponding one of the additional media contacts the workpiece while the workpiece is supported on the holding structure, wherein the controller is configured to, by the processor, selectively operate the additional powder removal devices independently to remove the powder material from the surface with the additional media while the workpiece is supported by the holding structure, wherein each of the first media and the additional media are different.

7. The system of claim 1, further comprising additional sensing devices within the enclosure, each of the additional sensing devices configured to detect one or more of additional surface characteristics of the workpiece while the workpiece is supported on the holding structure, wherein the controller is configured to, by the processor, detect the powder material on the surface of the workpiece based on the additional surface characteristics, wherein each of the first sensing device and the additional sensing devices comprise different sensing technology.

8. The system of claim 1, wherein the workpiece is produced by a powder- based additive manufacturing process.

9. A method, comprising:
   supporting a workpiece with a holding structure within an enclosure of a housing;
   housing, wherein supporting the workpiece with the holding structure includes retaining the workpiece in a basket of the holding structure;
   sensing surface characteristics of the workpiece with a first sensing device within the enclosure while the workpiece is supported by the holding structure;
   detecting, by a processor, a powder material on a surface of the workpiece based on the surface characteristics;
   selectively operating, by the processor, a first powder removal device within the enclosure to propel a first media toward the holding structure such that the first media contacts the workpiece while the workpiece is supported by the holding structure and thereby remove the powder material from the surface;
selectively controlling, by the processor, a frame within the enclosure supporting the first powder removal device to move the first powder removal device relative to the workpiece as supported by the holding structure; and
selectively controlling, by the processor, the frame to move the first powder removal device around the basket while operating the first powder removal device to propel the first media through a plurality of openings of the basket to contact the workpiece.

10. The method of claim 9, further comprising selectively controlling, by the processor, a frame within the enclosure supporting the first sensing device to move the frame relative to the workpiece as supported by the holding structure.

11. The method of claim 9, further comprising selectively operating, by the processor, additional powder removal devices within the enclosure to propel additional media toward the holding structure such that the additional media contacts the workpiece while the workpiece is supported by the holding structure and thereby remove the powder material from the surface, wherein each of the first media and the additional media are different.

12. The method of claim 9, further comprising sensing additional surface characteristics of the workpiece with additional sensing devices within the enclosure while the workpiece is supported by the holding structure, and detecting, by the processor, the powder material on the surface of the workpiece based on the additional surface characteristics, wherein each of the first sensing device and the additional sensing devices comprise different sensing technology.

13. The method of claim 9, further comprising generating a suction force sufficient to extract the powder material removed from the workpiece and the first media subsequent to the first media contacting the workpiece through an outlet of the enclosure with a suction device.

14. The method of claim 13, further comprising:
receiving the powder material and the first media from the outlet of the enclosure with a separation device; and
automatically separating the powder material and the first media with the separation device.

15. The method of claim 9, further comprising producing the workpiece by a powder-based additive manufacturing process.

16. A method, comprising:
supporting a workpiece with a holding structure within an enclosure of a housing;
sensing surface characteristics of the workpiece with a first sensing device within the enclosure while the workpiece is supported by the holding structure;
detecting, by a processor, a powder material on a surface of the workpiece based on the surface characteristics;
selectively operating, by the processor, a first powder removal device within the enclosure to propel a first media toward the holding structure such that the first media contacts the workpiece while the workpiece is supported by the holding structure and thereby remove the powder material from the surface;
selectively controlling, by the processor, a frame within the enclosure supporting the first powder removal device to move the first powder removal device relative to the workpiece as supported by the holding structure;
supporting the workpiece with a first robotic arm of the holding structure;
supporting the first powder removal device with a second robotic arm;
selectively operating, by the processor, the first robotic arm to move the workpiece relative to the first powder removal device and/or the first sensing device; and
selectively operating, by the processor, the second robotic arm to move the first powder removal device relative to the workpiece.

17. The method of claim 16, further comprising selectively operating, by the processor, additional powder removal devices within the enclosure to propel additional media toward the holding structure such that the additional media contacts the workpiece while the workpiece is supported by the holding structure and thereby remove the powder material from the surface, wherein each of the first media and the additional media are different.

18. The method of claim 16, further comprising generating a suction force sufficient to extract the powder material removed from the workpiece and the first media subsequent to the first media contacting the workpiece through an outlet of the enclosure with a suction device.

19. The method of claim 18, further comprising:
receiving the powder material and the first media from the outlet of the enclosure with a separation device; and
automatically separating the powder material and the first media with the separation device.

20. The method of claim 16, further comprising:
producing the workpiece by a powder-based additive manufacturing process;
selectively operating, by the processor, additional powder removal devices within the enclosure to propel additional media toward the holding structure such that the additional media contacts the workpiece while the workpiece is supported by the holding structure and thereby remove the powder material from the surface, wherein each of the first media and the additional media are different;
sensing additional surface characteristics of the workpiece with additional sensing devices within the enclosure while the workpiece is supported by the holding structure, and detecting, by the processor, the powder material on the surface of the workpiece based on the additional surface characteristics, wherein each of the first sensing device and the additional sensing devices comprise different sensing technology;
generating a suction force sufficient to extract the powder material removed from the workpiece and the first media subsequent to the first media contacting the workpiece through an outlet of the enclosure with a suction device;
receiving the powder material and the first media from the outlet of the enclosure with a separation device; and
automatically separating the powder material and the first media with the separation device.

* * * * *